United States Patent
te Poele et al.

(10) Patent No.: US 11,590,453 B2
(45) Date of Patent: *Feb. 28, 2023

(54) MEMBRANE DISINFECTANT

(71) Applicant: Diversey, Inc., Fort Mill, SC (US)

(72) Inventors: Sandy te Poele, Eindhoven (NL); Harry Kany, Hettenleidelheim (DE); Flemming Skou, Farum (DK); Marco Haag, Goenheim (DE)

(73) Assignee: Diversey, Inc., Fort Mill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/480,210

(22) Filed: Sep. 21, 2021

(65) Prior Publication Data

US 2022/0001337 A1 Jan. 6, 2022

Related U.S. Application Data

(62) Division of application No. 16/771,883, filed as application No. PCT/US2018/064279 on Dec. 6, 2018, now Pat. No. 11,185,825.

(60) Provisional application No. 62/599,072, filed on Dec. 15, 2017.

(51) Int. Cl.
| | | |
|---|---|---|
| *A01N 25/02* | (2006.01) | |
| *A01N 37/36* | (2006.01) | |
| *A61L 2/18* | (2006.01) | |
| *B01D 65/02* | (2006.01) | |

(52) U.S. Cl.
CPC ........... *B01D 65/022* (2013.01); *A01N 25/02* (2013.01); *A01N 37/36* (2013.01); *A61L 2/18* (2013.01); *B01D 2321/162* (2013.01); *B01D 2321/168* (2013.01)

(58) Field of Classification Search
CPC B01D 65/022; B01D 2321/162; A01N 37/36; C11D 3/0047
See application file for complete search history.

(56) References Cited

U.S. PATENT DOCUMENTS

| 9,206,059 B2 | 12/2015 | Brouwer et al. |
| 2003/0206882 A1 | 11/2003 | Richter et al. |
| 2006/0254624 A1 | 11/2006 | Zeiher et al. |
| 2008/0149570 A1 | 6/2008 | Zelher et al. |
| 2011/0182771 A1 | 7/2011 | Kany et al. |
| 2012/0237465 A1 | 9/2012 | Tamareselvey et al. |
| 2014/0367334 A1 | 12/2014 | Salonen et al. |
| 2015/0152364 A1 | 6/2015 | Theyssen et al. |
| 2017/0173642 A1 | 6/2017 | Li et al. |

FOREIGN PATENT DOCUMENTS

| CN | 103 143 262 A | 6/2013 | |
| EP | 1 444 316 A1 | 8/2004 | |
| WO | 83/00163 A1 | 1/1983 | |
| WO | WO-8300163 A1 * | 1/1983 | ............. C11D 1/146 |
| WO | 03/044145 A1 | 5/2003 | |

OTHER PUBLICATIONS

International Search Report and Written Opinion of priority Application No. PCT/US2018/064279 dated Aug. 1, 2019; 16 pages.
Biocides for Disinfection and Storage of Hydranautics Membrane Elements, Hydrauantics Nitto Group Co., Technical Service Bulletin, Mar. 2015, TSB110.12; 7 pages.

\* cited by examiner

*Primary Examiner* — Bradley R Spies
(74) *Attorney, Agent, or Firm* — Warunee Srisiri-Sisson

(57) ABSTRACT

A non-oxidizing, buffered disinfectant concentrate is provided to be included in a solution used to disinfect a membrane. The solution applied to the membrane is configured to have a pH that is compatible with the membrane. The disinfectant concentrate includes an aqueous solvent; a hydrotrope; a strong acid surface cleanser; a biocidal active, preferably, at least two biocidal actives; a buffer agent; and, optionally, an anionic surfactant. The biodical active may be selected to function both as a biocide and as a weak acid/buffer combination. A disinfectant solution applied to the membrane includes from about 0.1 wt % to about 3.5 wt % of this disinfectant concentrate.

18 Claims, 1 Drawing Sheet

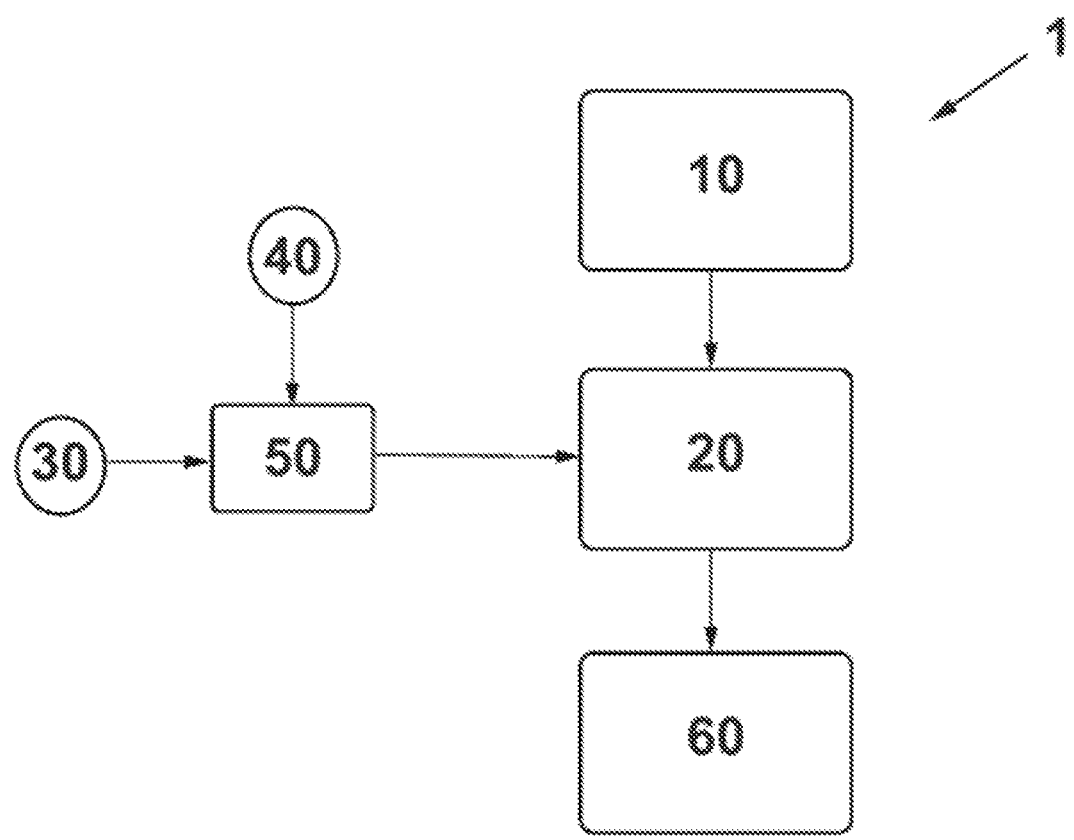

MEMBRANE DISINFECTANT

CROSS-REFERENCE TO RELATED APPLICATIONS

This application is a divisional of U.S. patent application Ser. No. 16/771,883, filed Jun. 11, 2020, which is a U.S. National Phase Application that claims the benefit and priority to the PCT International Application No. PCT/US2018/064279, filed on Dec. 6, 2018, which claims priority to U.S. Provisional Application No. 62/599,072, filed on Dec. 15, 2017; the content of these patent applications are incorporated herein by reference in their entireties.

FIELD OF INVENTION

The present invention relates to a disinfectant solution for use in a cleaning operation for a filtration membrane. The present invention also provides the method of using such a disinfectant solution.

BACKGROUND

Filtration is the separation of one material from another. Filtration may be affected by using a membrane. The material that is retained on the membrane is characterized as the retentate or concentrate. The liquid that passes through the membrane is the solute, filtrate or permeate, the latter being the term most commonly used with respect to membrane filtration.

Components remaining on the membrane after processing the stream is characterized as membrane fouling. Fouling results in a decline in flux and/or an increase in pressures over time causing the operation to have a decreased production. Membrane fouling is believed to occur due to a number of factors including electrostatic attraction, hydrophobic and hydrophilic interactions, the deposition and accumulation of feed components like suspended particulates, impermeable dissolved solutes, and even normally permeable solutes, on the membrane surface and/or within the pores of the membrane. These membrane filters must be subsequently subjected to a cleaning operation for the removal of any fouling that has occurred during the course of the treatment operation in order to continue to use such a filtration system to restore membrane capacity.

In dairy, brewing & beverage, processed food and water treatment operations, membrane plants are used for fractioning, purification, separation, and/or increasing the concentration of desired product components. Such membrane filters must then be subsequently subjected to a cleaning operation for the removal of any fouling that has occurred during the process.

Following the cleaning operation, microorganisms may still remain upon the membrane. It is necessary to recirculate and possibly soak the membrane in a disinfectant solution to further sanitize the membrane following the cleaning operation.

Conventionally, treatments having oxidized-based biocidal actives have been used to disinfect membranes. Commonly available disinfectants are often not compatible with the membrane as used in membrane filtration applications as these disinfectants may be harmful to the membrane materials. Oxidizing disinfectants may also be damaging to the membrane material, which limits their use.

Cleaning agents have been formulated to specifically address the nature and physicochemical properties of the foulants. These cleaning agents are formulated to attempt to break down the bonds that form between the foulants and the material the membrane is constructed from. The frequency of cleaning and type of chemical treatment performed on the membrane has been affects the operating life of a membrane, for example, through chemical degradation.

Cleaning and sanitizing filtration membranes is needed to comply with laws and regulations that require cleaning in certain applications (e.g., the food and biotechnology industries), reduce microorganisms to prevent contamination of the product streams, and improve the process operation by restoring flux and pressure.

While sanitizing and cleaning compositions for hard surfaces are well known in the art, their properties have not been generally known in the art to be compatible with cleaning membranes. For example, an acidic sanitizing and cleaning composition comprises a specific quaternary antimicrobial system consisting of C1-C4 hydroxyalkyl carboxylic acids, unsubstituted or substituted C5-C18 alkyl monocarboxylic acids, saturated or unsaturated C4 dicarboxylic acids, or additional inorganic or organic acids. While these solutions are known to be used in sanitizing and/or cleaning hard surfaces, such as a clean-in-place (CIP) and/or sanitize-in-place (SIP) process for cleaning and/or sanitizing plants in the food, dairy, beverage, brewery and soft drink industries, the acidic nature of the compounds would not generally be known in the art to be compatible with cleaning and/or sanitizing membranes.

Although various agents are known to prevent microbial growth, such as oxidizers, for example, there remains a need in the art to improve the prevention of microbial growth and biofilm formation on membranes. An additional, long-felt need in the art is the development of a disinfectant solution and a method of disinfecting a membrane that does not damage the membrane, but, rather, extends the life of the membrane.

Other advantages and features of the present invention become apparent to a person having ordinary skill in the art having the following specification taken in conjunction with the accompanying drawings.

SUMMARY

The present application relates to a non-oxidizing, buffered disinfectant solution for disinfecting membranes. The present application also relates to the use of such non-oxidizing, buffered disinfectant solution for disinfecting membranes.

An aspect of the present disclosure provides a non-oxidizing, buffered disinfectant concentrate solution comprising an aqueous solvent; a hydrotrope; a strong acid surface cleanser; a biocidal active, preferably, at least two biocidal actives; and a buffer agent. A disinfectant solution having the non-oxidizing, buffered disinfectant concentrate is configured to have a pH greater than about 1.8, wherein the disinfectant solution has from about 0.1 wt % to about 3.5 wt % of the non-oxidizing, buffered disinfectant concentrate based upon an overall weight of the solution.

In an embodiment of the present disclosure, the non-oxidizing, buffered disinfectant concentrate may have from about 3 to about 15 wt % of the strong acid surface cleanser, from about 0.5 to about 10 wt % of the hydrotrope, from about 1 to about 27 wt % of the biocidal active, and from about 1 to about 25 wt % of the buffer agent all based upon an overall weight of the non-oxidizing, buffered disinfectant concentrate.

In certain embodiments of the present disclosure, the non-oxidizing, buffered disinfectant concentrate additionally comprises an anionic surfactant. Further pursuant to this embodiment, the non-oxidizing, buffered disinfectant concentrate has from about 0.1 to about 10 wt % of the anionic surfactant based upon an overall weight of the composition. The anionic surfactant may be selected from any one of or any combination of a compound having a hydrophobic group of C6-22, and a water-solubilizing group of acid or salt form derived from sulfonic acid, sulfuric acid ester, phosphoric acid ester, carboxylic acid, ether carboxylic acid, cumene sulfonate, toluene sulfonate, and/or xylene sulfonate.

In some embodiments of the present disclosure, the biocidal active functions as a biocide and a weak acid. In an embodiment, the biocidal active of the non-oxidizing, buffered disinfectant concentrate includes a hydroxy acid. In certain embodiments, the biocidal active additionally includes a fatty acid. Further pursuant to these embodiments, the hydroxy acid may include at least one of citric acid, glycolic acid, salicylic acid and lactic acid, and the fatty acid includes any one of caproic acid, caprylic acid, capric acid, any salt thereof, and any combination thereof. Still, further pursuant to this embodiment, the buffered disinfectant concentrate has from about 1 to about 25 wt % of the hydroxy acid based upon an overall weight of the composition. Even still, further pursuant to this embodiment, the non-oxidizing, buffered disinfectant concentrate may comprise from about 0.1 to about 2 wt % of the fatty acid based upon an overall weight of the non-oxidizing, buffered disinfectant concentrate.

In an embodiment of present disclosure, the hydrotrope of the non-oxidizing, buffered disinfectant concentrate may include n-octenyl succinic acid or derivative, anhydride or salt thereof, or any combination thereof. In certain embodiments, the non-oxidizing, buffered disinfectant concentrate may include cumene sulfonate, toluene sulfonate, xylene sulfonate, or any combination thereof. In certain embodiments, the strong acid surface cleanser of the non-oxidizing, buffered disinfectant concentrate may include any one of a sulfonic acid having an alkyl group with no greater than 3 carbon atoms, methane sulfonic acid, nitric acid, sulfuric acid, phosphoric acid, hydrochloric acid, formic acid, or any combination thereof. In certain other embodiments, the buffer agent of the non-oxidizing, buffered disinfectant concentrate may include a weak acid to maintain the acidity (pH) of a solution near a chosen value. In preferred embodiments, the weak acid is selected from an organic acid, more preferably, citric acid, acetic acid, gluconic acid, glycolic acid, lactic acid, salicylic acid, any salt thereof, or any combination thereof.

In another aspect, the present disclosure provides a method of disinfecting a membrane including the following steps in this specific order: rinsing the membrane in or after a cleaning operation; at least one of recirculating over the membrane and soaking the membrane with a solution having a non-oxidizing disinfectant for about 5 to about 60 minutes; and post-rinsing the membrane for removal of the solution. In an embodiment of the present disclosure, the solution has a pH of greater than about 1.8 when applied to the membrane.

According to this aspect of the present disclosure, the non-oxidizing disinfectant may be configured according the specifications for the non-oxidizing, buffered disinfectant concentrate provided herein. In an embodiment of the present disclosure, the non-oxidizing disinfectant may be configured to function as a non-oxidizing descaler disinfectant. Further pursuant to this embodiment of the present disclosure, the membrane being disinfected may be used in any one of a dairy operation, a brewing operation, a beverage operation, a processed food operation, and a water treatment operation.

Other aspects and embodiments will become apparent upon review of the following description. The invention, though, is pointed out with particularity by the included claims.

BRIEF DESCRIPTION OF THE DRAWINGS

Having thus described the present disclosure in general terms, reference will now be made to the accompanying drawings, which are not necessarily drawn to scale, and wherein:

FIG. 1 is a flowchart showing the steps in a method of disinfecting a membrane according to an embodiment of the present disclosure.

DETAILED DESCRIPTION

The present present disclosure now will be described more fully hereinafter. Preferred embodiments of the present disclosure may be described, but this present disclosure may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the present disclosure are not to be interpreted in any way as limiting the invention.

As used in the specification and in the appended claims, the singular forms "a", "an", and "the" include plural referents unless the context clearly indicates otherwise. For example, reference to "a biocidal active" includes a plurality of such biocidal actives.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

As used herein, the term "biocidal active," which may additionally be referred to herein as a "disinfectant" or a "biocide," can refer to an antimicrobial agent, such as, for example, without intending to be limiting, a germicide, an antibiotic, an antibacterial, an antiviral, an antifungal, an antiprotozoal and an antiparasite.

As used herein, the term "buffer" means a compound that maintains the pH of the cleaning solution within a narrow range of limits. A buffer included in the cleaning solution of the present disclosure maintains a pH in a desired range.

As used herein, the term "hydrotrope" means a compound that helps other compounds become dissolved in a solvent. Due to this action, a hydrotrope may also be known as a solubilizer. Hydrotropy is a property that relates to the ability of a material to improve the solubility or miscibility of a substance in liquid phases where such substance tends to be only partly soluble or even insoluble altogether. Without being limited to a particular theory, a hydrotrope modifies a formulation to increase the solubility of an insoluble substance. Such combinations more favorably create micellar or mixed micellarformulations resulting in a stable emulsion or suspension of the partly soluble or insoluble substance. Certain hydrotropes may also have a surfactant type quality. Similar to surfactants, hydrotropes may be polar (hydrophilic) or non-polar (hydrophobic) in nature.

As used herein, the term "strong acid surface cleanser" means a highly acidic cleaning agents capable of effectively removing inorganic deposited materials on surfaces.

As used herein, the term "surfactant" means an active cleaning agent of a cleaning solution that may perform any combination of wetting and even penetrating the soil in the equipment to be cleaned, loosening deposited soils at the surface of the equipment, and emulsifying the soils to keep them suspended in solution for removal from the equipment. Surfactants tend to also reduce the surface tension in the cleaning solution. Surfactants may be selected that are polar or hydrophilic in nature, such as negatively charged or anionic surfactant. Surfactants may be selected that are non-polar or hydrophobic in nature, such as nonionic surfactants having no charge. Amphoteric surfactants that behaviors like anionic, cationic and nonionic surfactants, depending on pH, can also be used. Conventionally, surfactants have been chosen in cleaning solutions for a particular temperature of use.

As used herein, the term "weak acid" indicates a compound itself having an acidity or a compound when used in a mixture with any other compounds having a resulting activity that is insufficient to harm the membranes being treated using the compositions and the methods of the present disclosure. In certain, preferred embodiments of the invention, the weak acid comprises any one of citric acid, acetic acid, gluconic acid, glycolic acid, lactic acid, salicylic acid, any salt thereof, or any combination thereof.

In certain embodiments of present disclosure, a compound of a composition intended to be used to clean and disinfect a membrane may function as a biocide or biocidal active, as defined herein, and as a weak acid as defined herein. Non-limiting examples of compounds that may function as a biocide and a weak acid include citric acid, glycolic acid, any salt thereof, or any combination thereof.

As used herein, "vol %" refers to the percentage of a named compound based upon the volume of the compound relative to total volume of the solution the compound is embodied within unless expressly provided otherwise.

As used herein, "wt %" refers to the percentage of a named compound based upon the weight of the compound relative to total weight of the solution the compound is embodied within unless expressly provided otherwise.

An aspect of the present disclosure described herein relates to a non-oxidizing, buffered disinfectant for use in disinfecting membranes having an aqueous solvent, a hydrotrope, a strong acid surface cleanser, a biocidal active, a buffer agent, and, optionally, an anionic surfactant. In preferred embodiments, the composition is non-oxidizing, and a disinfectant solution having the composition has a pH greater than about 1.8. The non-oxidizing buffered disinfectant may be additionally referred to herein as a composition for disinfecting a membrane, a non-oxidizing disinfectant, a non-oxidizing disinfectant concentrate, and the like.

In disinfecting certain membranes, rigid limits exist on certain types of compounds that may be included in the disinfecting solution as well as an upper limit on temperature and/or lower and upper limits on pH. The disinfecting solutions of the present disclosure allows for these limitations to be met. In particular, one exemplary advantage of the disinfecting solutions of the present disclosure is that the composition could be composed without phosphorus and/or nitrogen and may be used in plant operations where phosphorus and/or nitrogen has been restricted.

In certain embodiments of the present disclosure, the disinfectant solution has from about 0.1 wt % to about 3.5 wt % of the composition based upon an overall weight of the solution.

Strong Acid Surface Cleanser. In an embodiment of the present disclosure, the composition for disinfecting a membrane may comprise from about 2 to about 20 wt %, from about 3 to about 15 wt %, from about 3 to about 11 wt %, or from about 4 to about 10 wt % of the strong acid surface cleanser based upon an overall weight of the composition.

In certain embodiments of the present disclosure, a strong acid surface cleanser may comprise any one or combination of an inorganic acid and an organic acid. In a preferred embodiment, the strong acid surface cleanser comprises a sulfonic acid having an alkyl group with no greater than 3 carbon atoms, methane sulfonic acid, nitric acid, hydrochloric acid, sulfuric acid, phosphoric acid, formic acid, or any combination thereof.

Hydrotrope. In an embodiment of the present disclosure, the composition for disinfecting a membrane may comprise from about 0.1 to about 15 wt %, from about 0.5 to about 10 wt %, from about 1 to about 7.5 wt %, and from about 1.5 to about 7.5 wt % of the hydrotrope based upon an overall weight of the composition.

In certain embodiments of the present disclosure, the hydrotrope comprises any one of n-octenyl succinic acid or derivative, anhydride or salt thereof. In certain embodiments, the hydrotrope may comprise any one or combination of cumene sulfonate, toluene sulfonate, and xylene sulfonate in addition to or instead of other hydrotropes in the composition for disinfecting a membrane.

Biocidal Active. In an embodiment of the present disclosure, the composition for disinfecting a membrane may comprise from about 0.5 to about 30 wt %, from about 1 to about 27 wt %, from about 2 to about 15 wt %, from about 2.5 to about 10 wt %, or from about 3 to about 8 wt % of the biocidal active, based upon an overall weight of the composition.

In a preferred embodiment of the present disclosure, the biocidal active comprises a hydroxy acid and a fatty acid. In certain embodiments, even more preferably, the hydroxy acid comprises at least one of citric acid, glycolic acid, salicylic acid and lactic acid. In still other embodiments, preferably, the fatty acid may comprise any one of caproic acid, caprylic acid, capric acid, any salt thereof, or any combination thereof.

Buffer Agent. In an embodiment of the present disclosure, the composition for disinfecting a membrane may comprise from about 1 to about 30 wt %, from about 1 to about 25 wt %, or from about 2 to about 20 wt % of the buffer agent based upon an overall weight of the composition. A buffer will assist with maintaining the pH of a solution comprising the composition for disinfecting a membrane that is compatible with the membrane. In a preferred embodiment, the pH of the solution comprising the composition for disinfecting a membrane is greater than about 1.8.

In an embodiment of the present disclosure, a buffer agent may be selected from a group consisting of: malonic acid, citric acid, tartartic acid, glutamic acid, benzylic acid, glutaric acid, gluconic acid, lactic acid, salicylic acid, malic acid, acetic acid, oxalic acid, phosphoric acid, carbonic acid, carbonic acid, formic acid, boric acid, and tetraboric acid.

In an embodiment of the present disclosure, the buffer agent may comprise an inorganic acid, an organic acid, any salts thereof, or any combination thereof. For example, the buffer agent may comprise phosphoric acid as a nonlimiting example, or a phosphate buffering agent, and, in a preferred embodiment, a weak acid or any salt thereof. In a preferred embodiment, the buffer comprises citric acid, acetic acid, gluconic acid, glycolic acid, lactic acid, salicylic acid, any salt thereof, or any combination thereof.

In certain embodiments of the present disclosure, compounds may be included that act as both a buffer agent and a biocidal active. In one embodiment, exemplary compounds capable of functioning as a combined buffer agent and/or weak acid and is also capable of functioning as a biocidal active include citric acid, glycolic acid, or any combination thereof.

A small amount of urea may be optionally employed in the compositions of the present disclosure. Organic degradation can occur in the presence of nitric acid by oxidation and nitration mechanisms due to the presence and oxidizing power of nitrogen dioxide ($NO_2$) and nitrogen tetroxide ($N_2O_4$), collectively referred to as nitrogen peroxide. Urea may be added to react with the nitrogen peroxide to reduce the nitrogen peroxide to nitrogen. Urea is useful in any amount effective to reduce the nitrogen peroxide to nitrogen.

Surfactant. In other embodiments of the present disclosure, the disinfectant solution may optionally comprise a surfactant. Surfactants may be included in the disinfectant solution for a variety of reasons including improved surface wetting by lowering the surface tension, improved soil or biofilm penetration, removal and suspension of organic soils, enhancement of biocidal effect, and/or increasing the solubility of the antimicrobial fatty acid in water by acting as a hydrotrope or coupling agent for the antimicrobial fatty acid to mention a few. One skilled in the art will understand that some surfactants or mixtures of surfactants serve one or more of these purposes better than others. The surfactant or mixture of surfactants selected will therefore impart different beneficial characteristics to the compositions depending on the selection made. The surfactants may be selected depending on the expected use, method of application, concentration, temperature, foam control, soil type, and so forth. The selection will of course also depend on the end use application of the composition. In an embodiment of the present disclosure, the composition for disinfecting a membrane may comprise from about 0.1 wt % to about 10 wt %, from about 0.5 wt % to about 8 wt %, from about 1 wt % to about 7 wt %, or from about 2 wt % to about 7 wt % of the surfactant based upon the overall weight of the composition.

The surfactants useful herein include nonionic and/or anionic surfactants. Most suitably, the surfactants employed include water soluble or water dispersible anionic or nonionic surfactants, or some combination thereof.

Anionic surfactants that may be included in the composition of the present disclosure may comprise, in non-limiting examples, carboxylates such as an alkyl carboxylate (e.g., in a non-limiting, example, a carboxylic acid salt), a polyalkoxycarboxylate, an alcohol ethoxylate carboxylate, a nonylphenol ethoxylate carboxylate, an alkyl ether carboxylic acid such as an alkyl (C8) ether (5EO) carboxylic acid), an alkyl (C8) ether (8EO) carboxylic acid, and a polyoxyethylene alkyl ether carboxylic acid; sulfonates such as an alkyl sulfonate, an alkylbenzene sulfonate, an alkylarylsulfonate, an alpha-olefinsulfonate, and a sulfonated fatty acid ester; sulfonic acids added using any sulfonic acid salt such as an alkane sulfonic acid whereby an alkane (C13-17) sulfonic acid is preferred in certain embodiments of the present disclosure; sulfates such as a sulfated alcohol, such as a fatty alcohol sulfate, a sulfated alcohol ethoxylate, a sulfated alkylphenol, an alkyl sulfate, a sulfosuccinate, and an alkyl ether sulfate; and/or phosphate esters such as an alkyl phosphate ester.

In a preferred embodiment of the present disclosure, the anionic surfactant comprises any one or more of a compound having a hydrophobic group of C6-22 such as alkyl, alkylaryl, alkenyl, acyl, long chain hydroxyalkyl, alkoxylated derivatives thereof and so forth; and at least one water-solubilizing group of acid or salt form derived from sulfonic acid, sulfuric acid ester, phosphoric acid ester, carboxylic acid, and/or ether carboxylic acids. The salt may be selected based on the specific formulation to which it is being added.

In some embodiments of the present disclosure, a nonionic surfactant is suitably employed to improve surface wetting, soil removal, and so forth. It may also function to improve the solubility of the fatty acids at use dilutions.

In an embodiment of the present disclosure, a solution used to disinfect the membrane comprises from about 0.1 wt % to about 3.5 wt % of the composition for disinfecting a membrane, also known as a concentrate, based upon an overall weight of the solution.

In a preferred embodiment of the present disclosure, a composition for disinfecting a membrane, or the concentrated composition, comprises from about 3 to about 15 wt % of the strong acid surface cleanser, from about 0.5 to about 10 wt % of the hydrotrope, from about 1 to about 27 wt % of the biocidal active, and from about 1 to about 25 wt % of the buffer agent all based upon an overall weight of the composition.

The composition may additionally comprise an anionic surfactant. Further pursuant to this embodiment of the present disclosure, the composition may comprise from about 0.1 to about 10 wt % of the anionic surfactant based upon an overall weight of the composition. Even further pursuant to this embodiment of the present disclosure, the anionic surfactant may comprise any one of a compound having a hydrophobic group of C6-22; and a water-solubilizing group of acid or salt form derived from sulfonic acid, sulfuric acid ester, phosphoric acid ester, carboxylic acid, and/or ether carboxylic acids; or any combination thereof.

In an embodiment of the present disclosure, the biocidal active comprises a hydroxy acid. The hydroxy acid, according to this embodiment, may comprise any one of citric acid, glycolic acid, salicylic acid, lactic acid, and any combination thereof. The biocidal active may comprise from about 1 to about 30 wt % or about 1 to about 27 wt % of the hydroxy acid based upon an overall weight of the composition.

In certain other embodiments of the present disclosure, the biocidal active additionally comprises a fatty acid. The fatty acid may comprise any one of caproic acid, caprylic acid, capric acid, any salt thereof, or any combination thereof. The biocidal active may comprise from about 0.1 to about 2 wt % of the fatty acid based upon an overall weight of the composition.

In these embodiments of the present disclosure, the hydrotrope of the composition may comprise n-octenyl succinic acid and derivative, anhydride and any salt thereof. In certain embodiments, the strong acid surface cleanser may comprise any one of a sulfonic acid having an alkyl group with no greater than 3 carbon atoms, methane sulfonic acid, nitric acid, hydrochloric acid, sulfuric acid, phosphoric acid, formic acid, or any combination thereof. Still further pursuant to these embodiments, the buffer agent may comprise any one of citric acid, acetic acid, gluconic acid, lactic acid, salicylic acid, any salt thereof, or any combination thereof For example, the membrane being disinfected may be used in any one of a dairy operation, a brewing operation, a beverage operation, a processed food operation, and/or a water treatment operation.

An aspect of the present disclosure, provides the use of the non-oxidizing, buffered disinfectant solution in disinfect a membrane. FIG. 1 is a flowchart showing the steps in a method of disinfecting a membrane according to an embodiment of the present disclosure. The method of disinfecting a membrane 1 includes the steps of rinsing the membrane either in a cleaning operation or following a cleaning operation 10 and at least one of recirculating over the membrane and soaking the membrane with a solution having a non-oxidizing disinfectant for about 5 to about 60 minutes 20. Any of the non-oxidizing disinfectant concentrations, as disclosed herein, may be use as the non-oxidizing disinfectant to disinfect a membrane.

The exemplary embodiment of FIG. 1 shows the non-oxidizing disinfectant 30 being mixed with a solvent 40 in a mixing operation 50 to form the solution that is introducing to the recirculating and/or soaking step 20. In certain embodiments, the solvent comprises an aqueous-based solvent. In still other embodiments, the solvent comprises water. Of course, in other embodiments, the solution having the non-oxidizing disinfectant may come pre-mixed. The solution may comprise from about 0.1 wt % to about 3.5 wt % of the non-oxidizing disinfectant based upon an overall weight of the solution. In a preferred embodiment, the solution has a pH of greater than about 1.8 when applied to the membrane.

In an embodiment of the present disclosure, the non-oxidizing disinfectant is a non-oxidizing descaler disinfectant. Without intending to be bound in any way, a descaler disinfectant is suitable for both cleaning and disinfecting a membrane, for example.

Another step in disinfecting the membrane 1 includes post-rinsing the membrane for removal of the solution 60.

In an embodiment of the present disclosure, the treatment of the inanimate object meets a European Union norm for disinfectant testing EN1276 and/or EN1650.

European norms for disinfection testing have been established to assist with confirming disinfectant products conform to a standard of quality. Such European standards allow for a minimum disinfectant requirement to be established. The Comité Europeo de Normalización (CEN) is an association that brings together the national standardization bodies of the member countries in an effort to improve safety, quality and reliability of products, services, and/or processes. CEN/TC 216, the Chemical Disinfectants and Antiseptics Committee of the CEN identifies test standards to measure the bactericidal efficacy of disinfectants for use in, for example, food, industrial, domestic and institutional areas. EN1276:2009 is an efficacy test identifying the minimum requirements for bactericidal efficacy of chemical disinfectant and antiseptic products that form a homogeneous, physically stable preparation when diluted with hard water or, in the case of ready-to-use products, with water. Under EN1276, products may only be tested at a concentration of 80% or less since some dilution is always produced by adding the test organisms and interfering substance. EN1276 applies to disinfectant products that are used in food, industrial, domestic and institutional areas excluding areas and situations where disinfection is medically indicated and excludes products used on living tissues except those for hand hygiene in the aforementioned areas.

EN1650 provides an efficacy test and the minimum requirements for fungicidal or yeasticidal efficacy of chemical disinfectant and antiseptic products that form a homogeneous, physically stable preparation when diluted with hard water or, in the case of ready-to-use-products, with water. As with EN1276, products may only be tested at a concentration of 80% or less since some dilution is always produced by adding the test organisms and interfering substance. Also, similar to EN1276, EN1650 applies to products that are used in food, industrial, domestic and institutional areas excluding areas and situations where disinfection is medically indicated and excluding products used on living tissues except those for hand hygiene in the above considered areas. Both EN1276 and EN1650 are consider phase 2/step 1 tests, which involve quantitative suspension testing.

EN1276 and EN1650 are the defined test procedures that were used in the evaluation of the performance of the samples in the examples that follow.

EXAMPLES

The present disclosure is further defined by reference to the following examples, which describe disinfectant solutions and methods for disinfecting a membrane operation according to the present disclosure, and the performance of such in a membrane disinfecting operation.

Example 1

Formulation 1, as shown in Table 1, is an exemplary formulation representative of disinfectant concentrate.

TABLE 1

| Formulation 1 | | |
|---|---|---|
| Compound | Functionality | Concentration, wt % |
| water | solvent | 69.50 |
| citric acid | buffer agent/biocidal active | 13.65 |
| methane sulfonic acid | strong acid surface cleanser | 5.95 |
| glycolic acid | buffer agent/biocidal active | 3.50 |
| caprylic acid | biocidal active | 0.75 |
| cumene sulfonate | hydrotrope/anionic surfactant | 4.80 |
| n-octenyl succinic anhydride | hydrotrope | 1.85 |

The performance of Formulation 1 when included in a disinfectant solution that was subject to EN 1276 and EN 1650 is shown in Table 2.

TABLE 2

| Micro Efficacy Results for Formulation 1 | | | |
|---|---|---|---|
| EN Test | Species | Pass Concentration vol % | pH |
| EN1276 clean conditions, 5 min, 20° C. | Escherichia coli | 0.5 | 2.63 |
| | Enterococcus hirae | 1.0 | 2.30 |
| | Pseudomonas aeruginosa | 0.5 | 2.63 |

TABLE 2-continued

Micro Efficacy Results for Formulation 1

| EN Test | Species | Pass Concentration vol % | pH |
|---|---|---|---|
| | Staphylococcus aureus | 1.0 | 2.30 |
| | Leuconostoc | 0.5 | 2.63 |
| | Lactobacillus brevis | 1.0 | 2.30 |
| | Bacillus cereus | 0.5 | 2.63 |
| EN1650 clean conditions, 15 min, 20° C. | Candida albicans | 1.5 | 2.00 |

Example 2

Formulation 2, as shown in Table 3, is another exemplary formulation representative of disinfectant concentrate.

TABLE 3

Formulation 2

| Compound | Functionality | Concentration, wt % |
|---|---|---|
| water | solvent | 80.97% |
| methane sulfonic acid | strong acid surface cleanser | 8.40% |
| glycolic acid | buffer/biocidal active | 3.50% |
| caprylic acid | biocidal active | 0.50% |
| cumene sulfonate | hydrotrope/anionic surfactant | 4.80% |
| n-octenyl succinic anhydride | hydrotrope | 1.83% |

The performance of Formulation 2 when included in a disinfectant solution that was subject to EN 1276 and EN 1650 is shown in Table 4.

TABLE 4

Micro Efficacy Results for Formulation 2

| EN Test | Species | Pass Concentration vol % |
|---|---|---|
| EN1276 sp4, clean conditions, 5 min, 20° C. | Escherichia coli | 0.75 |
| | Enterococcus hirae | 0.75 |
| | Pseudomonas aeruginosa | 0.75 |
| | Staphylococcus aureus | 0.75 |
| | Leuconostoc | 0.75 |
| | Lactobacillis brevis | 1.00 |
| | Bacillus cereus | 0.50 |
| EN1650 sp2, clean conditions, 15 min, 20° C. | Candida albicans | 1.50 |

Table 5 provides the pH of varying concentrations of Formulation 1 and Formulation 2 in reverse osmosis water and tap water.

TABLE 5 pH versus Concentration

| | Formulation 1 | | Formulation 2 | |
|---|---|---|---|---|
| Concentration wt % | Reverse Osmosis Water | Tap Water | Reverse Osmosis Water | Tap Water |
| 0.00 | 5.20 | 7.40 | 5.20 | 7.50 |
| 0.50 | 2.40 | 3.20 | 2.30 | 3.70 |
| 0.75 | | | 2.15 | 2.80 |
| 1.00 | 2.15 | 2.50 | 2.00 | 2.50 |
| 1.50 | 2.00 | 2.25 | 1.90 | 2.15 |
| 2.00 | 1.90 | 2.10 | 1.75 | 2.00 |
| 2.50 | 1.80 | 1.95 | 1.65 | 1.85 |
| 3.00 | 1.70 | 1.85 | 1.60 | 1.75 |
| 3.50 | 1.65 | 1.80 | 1.50 | 1.70 |

Example 3

A laboratory membrane filtration test set-up was used for membrane compatibility test on reverse osmosis (RO) membranes, which contained four (4) membrane cells with a membrane surface area of 10 cm$^2$ for each cell. Two (2) cells were used for each tested solution. New membrane material from the membrane supplier was used for each test. The test comprised the following steps:

(1) carefully cut pieces of reversed osmosis polyamide (PA) membrane material and put the pieces into the membrane cells;

(2) placed the membrane cells into the membrane unit;

(3) cleaned the virgin membrane with NaOH at pH 12, 30 min, 50° C. with a feed pressure of 9 bars;

(4) rinsed the membrane with soft water until the pH was neutral;

(5) prepared 2000 ppm of NaCl solution;

(6) measured the Clean Water Flux (CWF) with the 2000 ppm NaCl solution at 15 bar feed pressure and 25° C.;

(7) took samples of the feed solution and the permeate solution of each cell and measure the conductivity of the samples. Salt retention was calculated as equaled to:

(conductivity of the feed−conductivity of the permeate)/conductivity of the feed.

(8) rinsed the membranes with soft water;

(9) prepared one (1) liter of the solutions to be tested in beakers;

(10) took the membranes carefully out and stored store one membrane piece in one beaker of test solution;

(11) stored membranes in the test solution for 20 h at constant temperature (25° C.) and stirring;

(12) took the membrane carefully out the test solutions and carefully rinsed test solutions of the membrane by hand with soft water;

(13) placed the membranes back in the membrane cells;

(14) rinsed the membrane with soft water until pH was neutral;

(15) prepared 2000 ppm of NaCl solution;

(16) measured the CWF with the 2000 ppm NaCl solution at 15 bar feed pressure and 25° C.; and

(17) took samples of the feed solution and the permeate solution of each cell and measured the conductivity of the samples. Salt retention is calculated according to the equation provided above.

A laboratory membrane filtration test set-up was used for an ultrafiltration (UF) membrane, which contained four (4) membrane cells with a membrane surface area of 10 cm$^2$ for each cell. Two (2) cells were used for each tested solution. New membrane material from the membrane supplier was used for each test. The test comprised the following steps:

(1) carefully cut pieces of ultrafiltration polyethersulfone (PES) or polysulfone (PS) membrane material and put the pieces into the membrane cells;

(2) placed the membrane cells into the membrane unit;

(3) cleaned the virgin membrane with NaOH at pH 12, 30 min, 50° C. with a feed pressure of 1 bars;

(4) rinsed the membrane with soft water until the pH was neutral;

(5) measured the Clean Water Flux (CWF) with soft water at 2 bar feed pressure and 25° C.;

(6) prepared one (1) liter of the to be tested solutions in beakers;

(7) took the membranes carefully out the membrane cells and stored one membrane piece in one beaker of test solution;

(8) stored membranes in the test solution for 20 hours at constant temperature (25° C.) and stirring;

(9) took the membrane carefully out the test solutions and carefully rinsed test solutions of the membrane by hand with soft water;

(10) placed the membranes back in the membrane cells;

(11) rinsed the membrane with soft water until pH was neutral; and

(12) measured the CWF with soft water at 2 bar feed pressure and 25° C.

The results of membrane compatibility tests of Formulation 1 at a 1 wt % solution concentration compared to various acid and base solutions are provided in Tables 6, 7 and 8. The results in Table 6 show the relative CWF recovery after a 20 hour soak time for a reverse osmosis membrane constructed of polyamide.

TABLE 6

Membrane Compatibility Test
20 hours soak time, 25° C.
Reverse Osmosis Polyamide Membrane

| Solution | pH | Relative CWF Recovery |
|---|---|---|
| 1 wt % Formulation 1 Solution | 2.16 | 91 ± 5.9 |
| Nitric Acid Solution | 2.00 | 91 ± 6.4 |
| 125 ppm peracetic acid + 575 ppm hydrogen peroxide | | 83 ± 10.9 |
| 200 ppm sodium hypochlorite | | 81 ± 4.8 |

The results in Table 7 provide a comparison of the salt retention upon treatment without a soak and following 20 hour soak for the various solutions identified in Table 6.

TABLE 7

Salt Retention Test
Salt Rejection Measured with 2000 ppm NaCl
Reverse Osmosis Polyamide Membrane

| | | Rejection, % | | |
|---|---|---|---|---|
| Solution | pH | New Membrane | After 20 hr Storage in Solution | Change |
| 1 wt % Formulation 1 Solution | 2.16 | 94 ± 1.1 | 94 ± 0.4 | No |
| Nitric Acid Solution | 2.00 | 97 ± 1.8 | 97 ± 2.1 | No |
| 125 ppm peracetic acid + 575 ppm hydrogen peroxide | | 98 ± 0.3 | 92 ± 1.1 | Yes, decrease |

TABLE 7-continued

Salt Retention Test
Salt Rejection Measured with 2000 ppm NaCl
Reverse Osmosis Polyamide Membrane

| | | Rejection, % | | |
|---|---|---|---|---|
| Solution | pH | New Membrane | After 20 hr Storage in Solution | Change |
| 200 ppm sodium hypochlorite | | 98 ± 0.0 | 95 ± 1.3 | Yes, decrease |

The relatively low CWF recovery compared to the nitric acid solution and the change in salt retention indicate that the PA membrane material is not compatible with oxidizing disinfectant solutions, such as 200 ppm sodium hypochlorite, or solution having 125 ppm peracetic acid and 575 ppm hydrogen peroxide. Comparing the relative CWF recovery of the 1 wt % Formulation 1 solution with nitric acid solution revealed no difference. Additionally no change in salt retention was observed after 20 hours of storage in the 1 wt % Formulation 1 solution. Hence, the 1 wt % Formulation 1 solution is fully compatible with the RO polyamide membrane.

The results in Table 8 show the relative CWF recovery after a 20 hour soak time for an ultrafiltration (UF) membrane constructed of polyethersulfone.

TABLE 8

Membrane Compatibility Test
20 hours soak time, 25° C.
Ultrafiltration Polyethersulfone Membrane

| Solution | pH | Relative CWF Recovery |
|---|---|---|
| 1 wt % Formulation 1 Solution | 2.16 | 103 ± 14 |
| Nitric Acid Solution | 2.00 | 77 ± 10 |

The 1 wt % Formulation 1 solution was fully compatible with the UF membrane.

Example 4

In order to test the descaling properties of the Formulation 1, one liter of 1 wt % of Formulation 1 solution was prepared and 1 gram of tricalcium phosphate was added to this solution under stirring and at room temperature. The result was a clear solution and all tricalcium phosphate was dissolved, indicating that Formulation 1 can be used to dissolve tricalcium phosphate and thus has descaling properties.

Many modifications and other embodiments of the present disclosure set forth herein will come to mind to one skilled in the art to which this present disclosure pertains having the benefit of the teachings presented in the descriptions herein. It will be appreciated by those skilled in the art that changes could be made to the embodiments described herein without departing from the broad inventive concept thereof. Therefore, it is understood that this present disclosure is not limited to the particular embodiments disclosed, but it is intended to cover modifications within the spirit and scope of the present disclosure as defined by the included claims.

We claim:

1. A non-oxidizing disinfectant composition, comprises:
an aqueous solvent, a fatty acid in an amount of from about 0.1% to about 2% by weight based on total weight of the non-oxidizing disinfectant composition,
a hydroxy acid in an amount of from about 1% to about 25% by weight based on total weight of the non-oxidizing disinfectant composition,
a strong acid,
a buffer agent, and
a hydrotrope.

2. The composition of claim 1, wherein the fatty acid comprises caproic acid, caprylic acid, capric acid, any salt thereof, or any combination thereof.

3. The composition of claim 1, wherein the hydroxy acid comprises citric acid, glycolic acid, salicylic acid, lactic acid, or any combination thereof.

4. The composition of claim 1, wherein the non-oxidizing disinfectant composition comprises the strong acid in an amount of from about 3% to about 15% by weight based on total weight of the composition.

5. The composition of claim 1, wherein the strong acid comprises sulfonic acid having an alkyl group with no greater than three carbon atoms, methane sulfonic acid, nitric acid, sulfuric acid, hydrochloric acid, phosphoric acid, formic acid, or any combination thereof.

6. The composition of claim 1, wherein the non-oxidizing disinfectant composition comprises the buffer agent in an amount of from about 1% to about 25% by weight based on total weight of the composition.

7. The composition of claim 1, wherein the buffer agent comprises a weak acid.

8. The composition of claim 7, wherein the weak acid comprises citric acid, acetic acid, gluconic acid, glycolic acid, lactic acid, salicylic acid, any salt thereof, or any combination thereof.

9. The composition of claim 1, wherein the non-oxidizing disinfectant composition comprises the hydrotrope in an amount of from about 0.5% to about 10% by weight based on total weight of the composition.

10. The composition of claim 1, wherein the hydrotrope comprises cumene sulfonate, toluene sulfonate, xylene sulfonate, or any combination thereof.

11. The composition of claim 1, wherein the hydrotrope comprises: n-octenyl succinic acid, derivative, anhydride, or any salt thereof.

12. The composition of claim 1, further comprising an anionic surfactant.

13. The composition of claim 12, wherein the anionic surfactant is present in an amount of from about 0.1% to about 10% by weight based on total weight of the non-oxidizing disinfectant composition.

14. The composition of claim 12, wherein the anionic surfactant comprises a compound having a hydrophobic group of C6-22 and a water-solubilizing group of acid or salt form derived from sulfonic acid, sulfuric acid ester, phosphoric acid ester, carboxylic acid, an ether carboxylic acid, cumene sulfonate, toluene sulfonate, xylene sulfonate, or any combination thereof.

15. A non-oxidizing disinfectant solution obtained by diluting the non-oxidizing disinfectant composition of claim 1, with a diluent.

16. The non-oxidizing disinfectant solution of claim 15, wherein the diluent comprises water.

17. The non-oxidizing disinfectant solution of claim 15, wherein the solution comprises from about 0.1% to about 3.5% by weight of the non-oxidizing disinfectant composition based on total weight of the solution.

18. The non-oxidizing disinfectant solution of claim 15, wherein the solution has a pH greater than 1.8.

* * * * *